(12) United States Patent
Rao et al.

(10) Patent No.: US 10,943,147 B2
(45) Date of Patent: Mar. 9, 2021

(54) KNOWLEDGE-BASED ULTRASOUND IMAGE ENHANCEMENT

(71) Applicant: Siemens Medical Solutions USA, Inc., Malvern, PA (US)

(72) Inventors: Bimba Rao, San Jose, CA (US); Helene Houle, San Jose, CA (US); Bogdan Georgescu, Plainsboro, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 16/546,423

(22) Filed: Aug. 21, 2019

(65) Prior Publication Data

US 2019/0377978 A1    Dec. 12, 2019

Related U.S. Application Data

(63) Continuation of application No. 14/723,081, filed on May 27, 2015, now Pat. No. 10,430,688.

(51) Int. Cl.
G06K 9/00        (2006.01)
G06K 9/62        (2006.01)
A61B 8/00        (2006.01)
A61B 8/13        (2006.01)
(Continued)

(52) U.S. Cl.
CPC .......... *G06K 9/6256* (2013.01); *A61B 8/0891* (2013.01); *A61B 8/13* (2013.01); *A61B 8/463* (2013.01); *A61B 8/5269* (2013.01); *G06T 5/001* (2013.01); *G06T 2207/10132* (2013.01); *G06T 2207/20012* (2013.01); *G06T 2207/20076* (2013.01); *G06T 2207/20081* (2013.01);
(Continued)

(58) Field of Classification Search
CPC ... A61B 8/0891; A61B 8/5223; A61B 5/7264; A61B 8/488; A61B 2576/00; A61B 34/10; A61B 8/00; A61B 8/5215; G06T 2207/10132; G06T 2207/20081; G06K 9/46; G06K 9/6267; G06N 20/00
See application file for complete search history.

(56) References Cited

U.S. PATENT DOCUMENTS

| 5,040,225 A | 8/1991 | Gouge |
| 5,351,305 A | 9/1994 | Wood et al. |
| 5,479,926 A | 1/1996 | Ustuner et al. |

(Continued)

FOREIGN PATENT DOCUMENTS

| CN | 102551804 | 7/2012 |
| CN | 102855483 | 1/2013 |

(Continued)

OTHER PUBLICATIONS

Office Action dated May 3, 2019 in corresponding Chinese Patent Application No. 20160359329.6.

(Continued)

*Primary Examiner* — Guillermo M Rivera-Martinez

(57) ABSTRACT

Image enhancement is provided for medical diagnostic ultrasound. Knowledge-based detection of anatomy or artifact identifies locations to be enhanced. The knowledge-based detection of the locations may avoid identification of other anatomy or artifacts. The image enhancement is applied to the identified locations and not others.

19 Claims, 3 Drawing Sheets

(51) Int. Cl.
*A61B 8/08* (2006.01)
*G06T 5/00* (2006.01)

(52) U.S. Cl.
CPC ............ *G06T 2207/20192* (2013.01); *G06T 2207/30004* (2013.01)

(56) References Cited

U.S. PATENT DOCUMENTS

| | | | |
|---|---|---|---|
| 5,524,623 A * | 6/1996 | Liu | G01S 7/52077 600/447 |
| 6,398,733 B1 | 6/2002 | Simopoulos et al. | |
| 6,501,849 B1 | 12/2002 | Gupta | |
| 7,295,706 B2 | 11/2007 | Wentland et al. | |
| 7,648,460 B2 | 1/2010 | Simopoulos et al. | |
| 7,664,301 B2 | 2/2010 | Kim et al. | |
| 7,664,326 B2 | 2/2010 | Tamura | |
| 7,672,491 B2 | 3/2010 | Krishnan et al. | |
| 7,680,312 B2 | 3/2010 | Jolly et al. | |
| 7,747,054 B2 | 6/2010 | Zhou et al. | |
| 7,876,934 B2 | 1/2011 | Georgescu et al. | |
| 8,170,318 B2 | 5/2012 | Rao et al. | |
| 8,885,926 B2 | 11/2014 | Seung et al. | |
| 9,237,257 B1 * | 1/2016 | Szedo | H04N 5/142 |
| 9,629,615 B1 | 4/2017 | Tavakoli et al. | |
| 2005/0137479 A1 * | 6/2005 | Haider | A61B 8/06 600/440 |
| 2007/0055153 A1 * | 3/2007 | Simopoulos | G06F 19/321 600/437 |
| 2007/0083114 A1 | 4/2007 | Yang et al. | |
| 2009/0097723 A1 * | 4/2009 | Washburn | G06T 7/0012 382/128 |
| 2009/0226081 A1 * | 9/2009 | Zhou | G06T 7/12 382/159 |
| 2012/0078099 A1 * | 3/2012 | Suri | A61B 8/0891 600/440 |
| 2012/0215110 A1 * | 8/2012 | Wilkening | G01S 7/5209 600/453 |
| 2012/0243757 A1 * | 9/2012 | Funka-Lea | G06T 7/0002 382/131 |
| 2013/0034288 A1 | 2/2013 | Boyden et al. | |
| 2013/0303880 A1 | 11/2013 | Hsu | |
| 2013/0345566 A1 | 12/2013 | Weitzel et al. | |
| 2014/0046186 A1 * | 2/2014 | Mauldin, Jr. | A61B 8/4483 600/443 |
| 2014/0147013 A1 * | 5/2014 | Shandas | A61B 8/5246 382/107 |
| 2014/0194740 A1 | 7/2014 | Stein et al. | |
| 2014/0243614 A1 | 8/2014 | Rothberg et al. | |
| 2014/0363068 A1 * | 12/2014 | Hwang | G01S 7/52047 382/131 |
| 2015/0101411 A1 * | 4/2015 | Zalev | A61B 8/4281 73/643 |
| 2015/0379700 A1 | 12/2015 | Kamiyama et al. | |
| 2016/0242742 A1 | 8/2016 | Solsona et al. | |
| 2016/0242854 A1 | 8/2016 | Grass et al. | |

FOREIGN PATENT DOCUMENTS

| | | |
|---|---|---|
| JP | 2007530160 | 11/2007 |
| JP | 2010029281 | 12/2010 |
| JP | 2015514491 | 5/2015 |

OTHER PUBLICATIONS

Notice of Allowance dated Jun. 5, 2018 in corresponding Japanese Patent Application No. 2016-102512.

* cited by examiner

KNOWLEDGE-BASED ULTRASOUND IMAGE ENHANCEMENT

RELATED APPLICATION

This application is a continuation application of U.S. application Ser. No. 14/723,081, filed May 27, 2015, the entire contents of which are hereby incorporated by reference.

BACKGROUND

The present embodiments relate to medical diagnostic ultrasound imaging. In particular, ultrasound imaging is enhanced.

Traditional image enhancement algorithms are limited in their ability to perfect an ultrasound image. The image enhancement operates without specific prior knowledge of the anatomy and pathology represented in the image. Basic image processing techniques, such as low pass filters, reduce speckle noise but blur out anatomic structures.

In many cases, imaging artifacts have the same or similar properties to anatomic structures or tissue and hence are not detectable and effectively segmentable by image processing algorithms. The image processing may even enhance the artifacts. High pass filters used for edge enhancement enhance speckle noise. Techniques that are more complex rely on standard image analysis, such as gradient, variance, or simply amplitude-based image segmentation to process selectively various parts of the image. While these techniques work on simpler images, images with artifacts (e.g., clutter, side lobes, grating lobes, or rib shadows) or other anatomy with similar properties may not respond as desired to the complex techniques. For example, gradient edge detection finds edges of the desired anatomy for filtering or enhancement, but may treat the artifact as an edge, enhancing a portion of the image not to be enhanced.

BRIEF SUMMARY

By way of introduction, the preferred embodiments described below include methods, computer readable media, instructions, and systems for image enhancement in medical diagnostic ultrasound. Knowledge-based detection of anatomy or artifact identifies locations to be enhanced (e.g., increased, suppressed, or processed in any other way). The knowledge-based detection of the locations may avoid identification of other anatomy or artifacts. The image enhancement is applied to the identified locations and not others.

In a first aspect, a method is provided for image enhancement in medical diagnostic ultrasound. An ultrasound system acquires ultrasound image data from a scan of tissue of a patient. The ultrasound image data represents spatial locations of the tissue. A processor of the ultrasound system applies a machine-learnt classifier to the ultrasound image data. The machine-learnt classifier outputs locations of an imaging artifact of the ultrasound system in the ultrasound image data. The ultrasound image data is altered for the locations of the imaging artifact differently than for other locations. An ultrasound image of the tissue of the patient is displayed from the altered ultrasound image data.

In a second aspect, a non-transitory computer readable storage medium has stored therein data representing instructions executable by a programmed processor for image enhancement in medical diagnostic ultrasound. The storage medium includes instructions for receiving, from an ultrasound scanner, detected ultrasound data representing a patient, classifying locations represented by the detected ultrasound data, the classifying being with a knowledge base, enhancing the detected ultrasound data as a function of the classification of the locations, the enhancing changing amplitude of the ultrasound data for some of the locations relative to other locations while maintaining representation of all of the locations, and generating an image from the enhanced ultrasound data.

In a third aspect, a system is provided for image enhancement in medical diagnostic ultrasound. A receive beamformer is configured to acquire ultrasound data representing a region of a patient. A B-mode detector, Doppler estimator, or both are configured to output detected data from the ultrasound data. A processor is configured to extract input features from the detected data, identify an artifact from the detected data as a function of a knowledge base, and image process the detected data as a function of the artifact. A display is configured to display an image of the region based on the image processed detected data.

Further aspects and advantages of the invention are discussed below in conjunction with the preferred embodiments. The present invention is defined by the following claims, and nothing in this section should be taken as a limitation on those claims.

BRIEF DESCRIPTION OF THE DRAWINGS

The components and the figures are not necessarily to scale, emphasis instead being placed upon illustrating the principles of the invention. Moreover, in the Figures, like reference numerals designate corresponding parts throughout the different views.

DETAILED DESCRIPTION OF THE DRAWINGS AND PRESENTLY PREFERRED EMBODIMENTS

Knowledge-based enhancement of ultrasound images is provided. Knowledge-based feature detection techniques may successfully detect anatomic structures or artifacts in an ultrasound image without detecting other objects. These detection techniques are harnessed to improve and make smarter image processing or enhancement algorithms. Post-acquisition image enhancement benefits from application of knowledge-based detection. Already acquired image data may be altered by image processing localized specifically to detected anatomy or artifacts.

In one embodiment, imaging artifacts are identified for enhanced imaging. The knowledge is captured as expert user annotations of artifacts in a knowledge database. This knowledge significantly improves artifact detection and minimization. Utilizing knowledge-based detection algorithms to detect artifacts, such as grating lobes, side lobes from rib reflections, rib shadows, other shadows, or spontaneous contrast, provides focused image enhancement. The output of the knowledge-based algorithms is used for improved image processing to remove a captured artifact.

Figure 1:
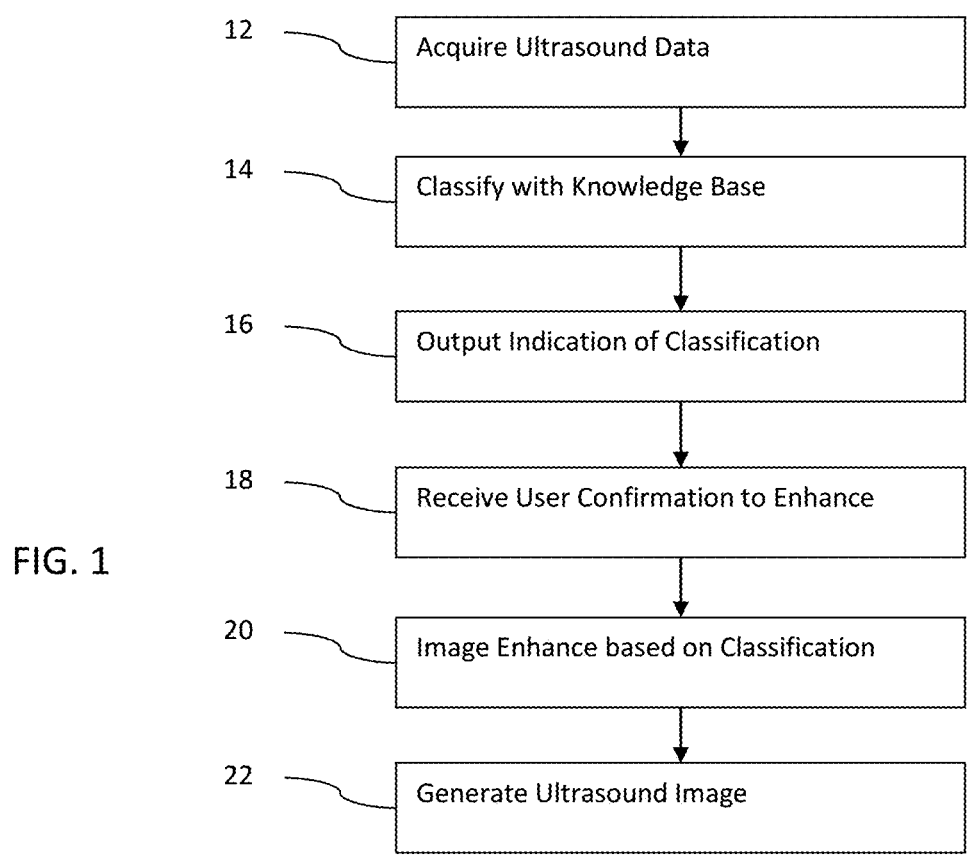
FIG. 1 is a flow chart diagram of one embodiment of a method for image enhancement in medical diagnostic ultrasound.

FIG. 1 shows one embodiment of a method of image enhancement in medical diagnostic ultrasound. This embodiment is directed to detecting anatomy or artifacts using knowledge-based detection. A collection of expert annotated examples is used to identify more accurately locations of anatomy or artifacts. Imaging from the already acquired data is enhanced by processing differently for the identified locations than for other locations. Image enhancement is improved by the detection provided with a knowledge base.

Additional, different, or fewer acts may be provided. For example, acts 16 and 18 are not provided. As another example, acts for activating and/or configuring the ultrasound scanning are provided. The acts are directed to application of the knowledge base. Acts for creating and learning from the knowledge base may be provided in alternative or additional embodiments. The acts are performed in the order shown or a different order.

In act 12, an ultrasound system acquires ultrasound data from a scan of tissue of a patient. The ultrasound data represents the patient. A medical diagnostic ultrasound system applies electrical signals to a transducer, which then converts the electrical energy to acoustic energy for scanning a region of the patient. Echoes are received and converted into electrical signals by elements of the transducer for receive operation of the scan. Any type of scan, scan format, or imaging mode may be used. For example, harmonic imaging is used with or without added contrast agents. As another example, B-mode, color flow mode, spectral Doppler mode, M-mode, or other imaging mode is used.

Ultrasound data representing anatomical information is acquired from a patient. The ultrasound data represents a point, a line, an area, or a volume of the patient. Waveforms at ultrasound frequencies are transmitted, and echoes are received. The acoustic echoes are converted into electrical signals and beamformed to represent sampled locations within a region of the patient.

The beamformed data may be filtered or otherwise processed. In one embodiment, the ultrasound data is B-mode data representing tissue structures. The beamformed data is detected, such as determining an intensity (e.g., B-mode or backscatter power or intensity). In another embodiment, the ultrasound data is flow or motion data for locations associated with a vessel, flow, or tissue motion. A sequence of echo signals from a same location may be used to estimate velocity, variance, and/or energy as the detection. Echoes at one or more harmonics of the transmitted waveforms may be processed. The detected values may be filtered and/or scan converted to a display format. The ultrasound data representing the patient is post detection data, such as detected data before spatial and/or temporal filtering, filtered data before scan conversion, scan converted data before display mapping, or display mapped image data before or after output to a display.

The ultrasound imaging system is a scanner that provides the detected ultrasound data representing the patient. The ultrasound system receives the detected ultrasound data, such as receiving B-mode data, as an output from the detector. A processor of the scanner or a remote processor not part of the scanner receives the detected ultrasound data for knowledge-based detection.

In act 14, a knowledge base is used to classify locations in the received ultrasound data. The classifier is applied to each location represented by the data or is applied to distinguish between different locations. A processor classifies different locations represented by the ultrasound data as belonging to a class or not. Other classifiers than binary classifiers may be used, such as classifying each location as being a member of one of three or more classes (e.g., (1) background, artifact, and anatomy; (2) fluid, bone, and tissue; or (3) organ of interest, other organ, and non-determinative). Different locations belong to different classes. Some locations may belong to the same class. The classifier detects which locations are members of a class, such as detection of the locations of particular anatomy or of a particular artifact.

The processor classifies with a knowledge base. The knowledge base includes ground-truth labeled sets of ultrasound data. An expert annotates ultrasound images as including or not including the class and the locations that include the class. For example, tens, hundreds, or thousands of B-mode images with an artifact are annotated to indicate the location of the artifact. Another set of images without the artifact may be provided. As another example, a database of images is labeled for one or more anatomical structures. The database of images is created by an expert user analyzing images and annotating the images for the corresponding structures, features, and/or artifacts.

To classify with the knowledge base, one or more database images are identified and used to detect the structure in a current image as part of classification. The identified database images are also used to determine the shape or locations of the anatomical structure of interest.

The processor uses the knowledge base in classification by finding an image from the knowledge base most or sufficiently similar to the ultrasound data received in act 12. Cross-correlation, minimum sum of absolute differences, other correlation, or other similarity measure may be used. Scaling and/or spatial transformation may be applied to relate locations from the current frame of ultrasound data to the images of the knowledge base. The resulting knowledge base image is annotated to show the locations for the anatomy or artifact. The current frame of ultrasound data is labeled accordingly (i.e., corresponding locations identified as the anatomy or artifact). Other knowledge-based classification may be used.

In another embodiment, the processor uses the knowledge base by applying a machine-learnt classifier. The machine-learnt classifier is learnt from the database of annotated images. The annotated or ground-truth labeled images are used as training data. A processor learns the classification based on the ground truth and features extracted from the images of the knowledge base. Through one or more various machine-learning processes, the classifier is trained to detect locations of the anatomy and/or artifact.

Any features may be used for training and application. Haar wavelets, steerable features, directional features, machine-learnt features, and/or pattern matches are extracted from the image data for each location. A kernel of any size and/or shape is centered or positioned based on the location for which the feature is being extracted. The feature extraction occurs for each of the locations.

Any machine-learning algorithm or approach to classification may be used. For example, a support vector machine (e.g., 2-norm SVM), linear regression, boosting network, probabilistic boosting tree, linear discriminant analysis, relevance vector machine, neural network, Bayesian network, combinations thereof, or other now known or later developed machine learning is provided. Binary, hierarchal, or other learning processes may be used. Supervised or semi-supervised training may be used.

The machine learning provides a matrix or other output. The matrix is derived from analysis of the database of training data with known results. The machine-learning algorithm determines the relationship of different inputs to the result. The learning may select only a sub-set of input features or may use all available input features. A programmer may influence or control which input features to use or other performance of the training. For example, the programmer may limit the available features to information available in a given type of ultrasound imaging. The matrix associates input features with outcomes, providing a model for classifying. Machine training provides relationships using one or more input variables with outcome, allowing for verification or creation of interrelationships not easily performed manually.

The model represents a probability of a location represented by ultrasound data being of the class or not. This probability is a likelihood of membership in the class. A range of probabilities associated with different possible states (e.g., binary or a three or more possible states) is output. Alternatively, the class of the location is assigned based on the highest probability. In other embodiments, the class per location is output without probability information.

For application of the classifier, a same or different processor extracts discriminative input features from the received ultrasound data or data derived from the ultrasound data (e.g., filtered or parameterized data). An input feature vector of information is input to the classifier. The values of the input features are applied to the machine-learnt classier. The processor of the ultrasound system or other processor applies the classifier to the received ultrasound data to determine locations of the anatomy and/or artifact. The processor applies a matrix or other classifier construction to output the class of each of a plurality of locations represented by the ultrasound data. Locations of an anatomic structure or locations of an artifact are output based on the knowledge base incorporated into the machine-learnt classifier.

In one embodiment, an artifact is detected. Any artifact may be detected. The artifact is caused by the ultrasound system scanning, such as being due to a transducer characteristic, a scan format, scanning parameters, or image processing. Alternatively, the artifact is caused by anatomy, such as due to aberration or reflection. The artifact presents as a false object, shadowing, or other information not representative of actual anatomy at the location or representative of anatomy not to be detected.

Figure 2:
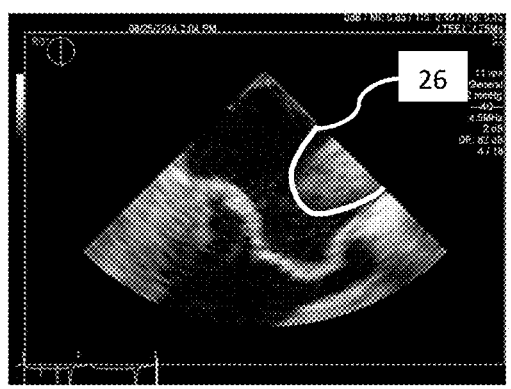
FIG. 2 is an example image of a heart with a grating lobe artifact.

For example, the ultrasound data represents one or more grating lobes. The classifier detects the location of any grating lobes. Using a knowledge base of images with and without grating lobes for a same application (e.g., heart imaging) and/or configuration (e.g., transducer, frequency, scan format, or other), grating lobe artifacts are detected in the ultrasound data. FIG. 2 shows an example image of a heart. A grating lobe causes a tissue representation in a fluid region. The area delineated at 26 shows the grating lobe. An image segmentation algorithm may identify the grating lobe as tissue instead of an artifact. To avoid aggressive enhancement approaches making alteration of the wrong data, the classifier detects the locations with intensity caused by the grating lobe as distinguished from other objects.

Figure 4:
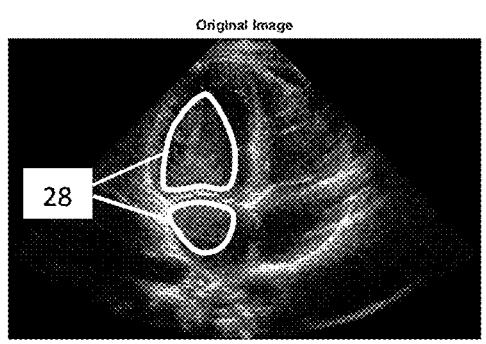
FIG. 4 is an example image of the heart with spontaneous contrast from blood.

As another example, the ultrasound data represents one or more regions of spontaneous contrast of blood cells. The spontaneous contrast is B-mode response to blood, such as blood in a heart chamber. Traditional ultrasound systems do not detect response from blood for B-mode imaging. Modern ultrasound machines are sensitive enough to pick up signals from blood circulating in the heart chamber. While this speaks to the high quality of ultrasound acquisition, the signal from blood may be distracting to the user trying to assess anatomy in a B-mode image. These spontaneous contrast characteristics of signal from blood are close enough to that from tissue, that image enhancements may treat the blood like tissue. FIG. 4 shows an example four-chamber view of the heart. The spontaneous contrast occurs primarily in two of the chambers. The areas delineated as 28 show the spontaneous contrast. The spontaneous contrast in the left ventricle (upper chamber) may be particularly distracting. The classifier detects the locations with intensity caused by the spontaneous contrast. The detection may be of all locations (e.g., both chambers noted in FIG. 4) or less than all locations (e.g., just the spontaneous contrast in the left ventricle).

In other examples, the ultrasound data represents shadowing. A region of dense tissue or bone may at least partially block ultrasound scanning from part of or the entire array, causing shadowing. In yet another example, bone causes lobe like artifacts due to reflecting or redirecting ultrasound data (e.g., acting as a mirror for acoustic energy). The classifier detects one or more of these artifacts. Other artifacts may be detected by the classifier.

In additional or alternative embodiments, one or more anatomical structures are detected by the classifier. The classifier is trained to detect any anatomical structure or part of anatomy, such as detecting the liver, heart, valve, left ventricle, or other anatomy. More than one anatomical structure may be located. A collection of features or a single feature occurring with respect to no specific anatomy or with respect to different anatomy may be detected.

Different classifiers are trained for different artifacts and/or anatomy. The same or different classifiers may be trained for different imaging situations, such a classifier for detecting a grating lobe artifact for imaging the heart and a different classifier for detecting a grating lobe artifact for imaging the liver. Configuration specific classifiers may be trained, such as one classifier for use with one transducer and corresponding frequency and another classifier for use with a different transducer and corresponding frequency. The same or different classifiers may be trained to detect different objects, such as one classifier for detecting an artifact and another classifier for detecting anatomy.

Referring again to FIG. 1, the processor outputs an indication of the locations in act 16. An image is generated from the ultrasound data. The detected locations for a given anatomy or artifact are indicated in the image, such as by color, line graphic, probability map, or intensity. The image enhancement of act 20 is to be performed after receiving user confirmation in act 18 of the accuracy of the detection of act 14. The ultrasound system processes the image after revealing the output of the machine-learnt classifier. The knowledge-based image processing is made transparent to the user. The user is informed what is to be altered and why before the processor automatically alters large parts of an image. The user may edit the detection, such as changing the classification of one or more locations. The confirmation by the user in act 18 is a key press or other solicited confirmation. The confirmation may be optional.

In act 20, the processor, filter, ultrasound system, or combinations thereof enhances the detected ultrasound data as a function of the classification of the locations. In segmentation, detected data is removed or isolated. For image enhancement, the background, other tissue, fluid, other object, or other representation by the ultrasound data remains. Instead, the ultrasound data is altered to make some locations more visible relative to other locations, to fill in gaps, to enlarge, to reduce, to separate, and/or otherwise image process the already detected data. The image processing for some locations is different than imaging processing for other locations. The enhancement changes the amplitude of the ultrasound data for some locations more or less relative to other locations while maintaining representation of all of the locations. Some locations may be represented by zero or background values due to the alteration, but are still represented locations.

Rather than applying image-processing algorithms relying on statistical tools to find locations that may be anatomy, the knowledge base is used to identify the locations. For example, locating gradients as an indication of an edge for filtering differently along the edge relies on statistics that certain gradients are edges. Artifacts or other anatomy may have similar gradients, so improperly enhanced. Using the knowledge base detection identifies the locations to which the different image processing (e.g., low pass filtering along and high pass filtering perpendicular to an edge) is applied. Edges of artifacts or other anatomy are not enhanced as much, in the same way, or at all. These detected locations are used in image processing for smarter and better image enhancement. Similarly, image processing to reduce or remove artifacts is applied just to artifact locations rather than all locations with similar statistical properties as the artifact.

Any image enhancement may be applied to the ultrasound data. For example, spatially adaptive filtering is applied. One or more characteristics of the filter adapt to the classification of the locations. The spatial filter kernel (e.g., size and/or weights) or type of filtering varies depending on the classification of the location being filtered. Anatomy or a border of anatomy may be enhanced for more or less filtering as compared to other locations. Edge detection, spatial filtering, temporal filtering, transformation, or other image process may vary as a function of location of the anatomy and/or artifact identified by the classifier.

In one embodiment, the enhancement is through removal or reduction of an artifact. For example, a high pass filter or amplitude scaling (e.g., reduction by an amount or %) is applied to locations associated with an artifact and not applied to or applied differently to other locations represented by the ultrasound data.

In a grating lobe example, the grating lobe information is suppressed. FIG. 2 shows a grating lobe generally indicated at 26 in the left ventricle. The grating lobe may be distracting to the user. After high pass filtering and/or amplitude scaling, the intensities caused by the grating lobe are reduced as reflected in FIG. 3. The aesthetics and/or diagnostic utility of the image may be improved. The characteristics of the grating lobe are not different from those of the rest of diagnostic tissue, making general application of adaptive filtering based on characteristic of the ultrasound data without reference to knowledge-based detection difficult or not as effective. Using knowledge-based detection, only the locations of the artifact are suppressed by an amount sufficient to make the artifact less or not visible.

Figure 5:
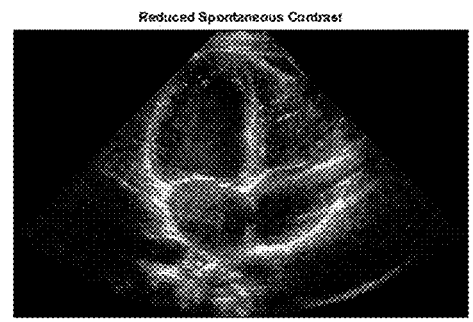
FIG. 5 is an example image of the heart of FIG. 4 enhanced to remove or reduce the spontaneous contrast from blood.

In another embodiment, amplitude scaling (e.g., reduction) or greater temporal persistence is applied to locations classified as spontaneous contrast. Different scaling (e.g., lesser), no scaling, or different persistence is applied to other locations. As seen in FIG. 4, the spontaneous contrast in the left ventrical may be distracting to the user. After amplitude scaling or temporal persistence, the spontaneous contrast is suppressed for the left ventricle as shown in FIG. 5. The spontaneous contrast in the other heart chamber is or is not also suppressed. Knowledge-based detection allows for distinguishing between locations for the same artifact. In the example of FIG. 5, the suppression is only for the spontaneous contrast in the left ventricle and not for other spontaneous contrast or the heart wall tissue. The suppression of the knowledge base detected artifact improves aesthetics and/or diagnostic utility of the image. Alternately, the spontaneous contrast may be emphasized and not suppressed if so desired by the user. The spontaneous contrast may be presented with a separate color map to distinguish spontaneous contrast from the rest of the anatomy.

Other artifacts, such as shadowing, may be processed differently for image enhancement. For example, shadowing is scaled or persisted more than for other locations in order to reduce the shadowing by increasing the intensities in the shadow.

In another embodiment, the ultrasound data is filtered differently by location based on detected anatomic structure. The detection using the knowledge base provides an overall or comprehensive structure definition and continuity. It is often difficult for image processing algorithms to determine whether or not two distinct pixels belong to the same anatomic structure, especially in images with high levels of noise and clutter. If the image enhancement more aggressively connects possible pixels or voxels by an overall setting, locations not part of the anatomy may be included. Using detection techniques based on an expert created database may allow the image processing algorithms to be much more aggressive in building structure continuity since there is increased confidence in knowing which pixels to process.

Any identified artifacts or anatomy may be enhanced by any location adaptive image processing. The location classification is used to adapt spatially the image enhancement. Specific anatomy, artifacts, and/or features may be suppressed, emphasized, or altered relative to other tissue, fluid, or structure represented by the ultrasound data. After or before anatomy or artifact specific enhancement, further image processing not specific to the detected anatomy or artifact may be applied.

In act 22, an image is generated. The processor or ultrasound system generates the image form the enhanced ultrasound data. Where the enhancement is applied to display values (e.g., RGB values), the ultrasound data is presented on the display. Where the enhancement is applied before mapping, such as after detection, scan conversion and/or mapping to display values is provided. The result is then output to a display.

The generated image is a B-mode, color flow mode, M-mode, pulsed wave Doppler, contrast agent, harmonic, other ultrasound image, or combination thereof. The image represents the patient at a given time or over time. The image may represent one or more sample locations within the patient, such as a planar or volume region.

Figure 3:
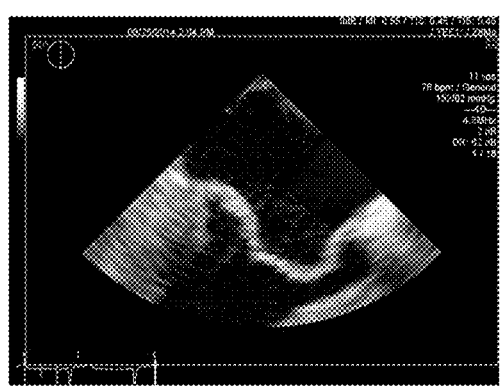
FIG. 3 is an example of the image of the heart of FIG. 2 enhanced to remove or reduce the grating lobe through image processing.

The image represents the patient without segmentation. Rather than isolating information, the entire scan region is represented in the image. One or more artifacts are suppressed and/or one or more anatomical locations are emphasized in the image by the enhancement. As compared to an image generated with the ultrasound data without the knowledge-based enhancement, less artifacts may be presented to the user, such as shown in FIGS. 3 and 5. Where both artifact suppression and anatomy of interest emphasis are provided, the displayed ultrasound image provides less distracting artifacts and more focus on the anatomy of interest.

Figure 6:
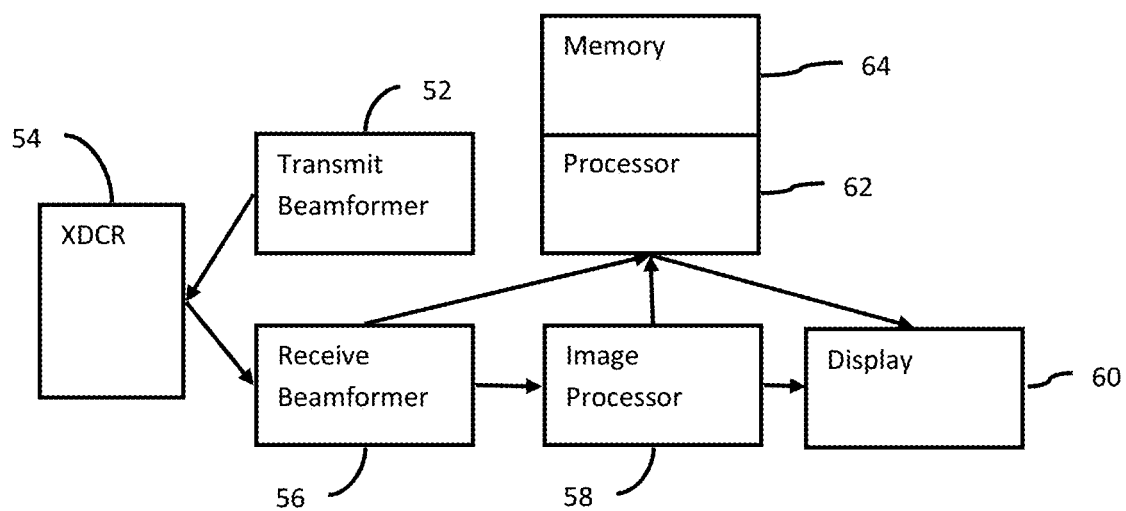
FIG. 6 is a block diagram of one embodiment of a system for image enhancement in medical diagnostic ultrasound.

FIG. 6 shows one embodiment of a system for image enhancement in medical diagnostic ultrasound. Knowledge-based detection of anatomy and/or artifacts is used to enhance selectively the acquired ultrasound data. The image processing performed by the system adapts to detected anatomy and/or artifacts. The system performs the method described above for FIG. 1 or a different method.

The ultrasound system includes a transmit beamformer 52, a transducer 54, a receive beamformer 56, an image processor 58, a display 60, a processor 62 and a memory 64. Other systems may be used. Additional, different or fewer components may be provided. For example, separate detectors and a scan converter are also provided. As another example, a user input device (e.g., mouse and/or keyboard) is provided for accepting user selection of an imaging application (e.g., cardiac imaging), configuration, and/or confirmation of detection. The detector may use one or more input features from other sources than the ultrasound data. Other sources of data may include sensors, a therapy system, or other inputs. Such devices or inputs may be provided to the processor 62 or the memory 64. In one embodiment, all of the input features used by the detector are acquired from ultrasound data.

The system 10 is a medical diagnostic ultrasound imaging system. Imaging includes two-dimensional, three-dimensional, B-mode, Doppler, color flow, spectral Doppler, M-mode, strain, elasticity, harmonic, contrast, or other imaging modalities now known or later developed. The ultrasound system 10 is a full size cart mounted system, a smaller portable system, a hand-held system, or other now known or later developed ultrasound imaging system. In another embodiment, the processor 62 and memory 64 are part of a separate system. For example, the processor 62 and the memory 64 are a workstation or personal computer operating independently of or connected with the ultrasound system. As another example, the processor 62 and the memory 64 are part of a therapy system.

The transducer 54 is a single, one-dimensional, multi-dimensional or other now known or later developed ultrasound transducer. Each element of the transducer 54 is a piezoelectric, microelectromechanical, capacitive membrane ultrasound transducer, or other now known or later developed transduction element for converting between acoustic and electrical energy. Each of the transducer elements connect to the beamformers 52, 56 for receiving electrical energy from the transmit beamformer 52 and providing electrical energy responsive to acoustic echoes to the receive beamformer 56.

The transmit beamformer 12 is one or more waveform generators, amplifiers, delays, phase rotators, multipliers, summers, digital-to-analog converters, filters, combinations thereof, and other now known or later developed transmit beamformer components. The transmit beamformer 52 is configured into a plurality of channels for generating transmit signals for each element of a transmit aperture. The transmit signals for each element are delayed and apodized relative to each other for focusing acoustic energy along one or more scan lines. Signals of different amplitudes, frequencies, bandwidths, delays, spectral energy distributions or other characteristics are generated for one or more elements during a transmit event.

The receive beamformer 56 is configured to acquire ultrasound data representing a region of a patient. The receive beamformer 56 includes a plurality of channels for separately processing signals received from different elements of the transducer 54. Each channel may include delays, phase rotators, amplifiers, filters, multipliers, summers, analog-to-digital converters, control processors, combinations thereof and other now known or later developed receive beamformer components. The receive beamformer 56 also includes one or more summers for combining signals from different channels into a beamformed signal. A subsequent filter may also be provided. Other now known or later developed receive beamformers may be used. Electrical signals representing the acoustic echoes from a transmit event are passed to the channels of the receive beamformer 56. The receiver beamformer 56 outputs in-phase and quadrature, radio frequency or other data representing one or more locations in a scanned region.

The receive beamformed signals are subsequently detected and used to generate an ultrasound image by the image processor 58. The image processor 58 is a B-mode/M-mode detector, Doppler/flow/tissue motion estimator, harmonic detector, contrast agent detector, spectral Doppler estimator, combinations thereof, or other now known or later developed device for outputting detected ultrasound data. The detection determines a characteristic of the acoustic response of the patient from the beamformed data. The image processor 58 may include a scan converter, buffer for display mapping, and/or the processor 62 for image enhancement. The detected or estimated signals, prior to or after scan conversion, may be used by the processor 62.

The processor 62 is a control processor, filter, general processor, application specific integrated circuit, field programmable gate array, digital components, analog components, hardware circuit, combinations thereof and other now known or later developed devices for image processing to enhance an image. The processor 62 is configured, with computer code, firmware, and/or hardware, to identify anatomy or artifacts represented in the detected data and alter the detected data to emphasize or suppress the anatomy or artifact.

The processor 62 receives, requests, and/or calculates values for the input features to be used by knowledge-based anatomy or artifact detection. In one embodiment, one or more of the features and corresponding values are extracted from the ultrasound data. The processor 62 performs one or more measures of data characteristics for a region around each of various locations represented by the ultrasound data. For example, Haar wavelet features provide one or more different measures for each location represented by the ultrasound data.

The processor 62 is configured to identify an artifact and/or anatomy from the detected data as a function of a knowledge base. In one embodiment, the knowledge base is represented as a machine-learnt classifier. The machine-learnt classifier is learned from the knowledge base. Feature values are extracted and input to the classifier. The classifier relates the features to class membership (i.e., artifact and/or anatomy) for each location. Different classifiers may be provided for different artifacts, anatomy, and/or applications (e.g., cardiac or radiology). In one embodiment, the classifier is a matrix trained to identify the artifact as a grating lobe, shadow, or spontaneous contrast of blood. In alternative embodiments, other knowledge base identification is used, such as using matching of current ultrasound data with one of many annotated images in a database.

The processor 62 and/or the image processor 58 are configured to image process the detected data as a function of the artifact and/or anatomy. The locations associated with the detected object are handled or image processed differently than other locations. Different filtering, edge enhancement, or other image process is applied to locations of the detected class than other locations. The difference may be in settings (i.e., apply filtering but with different characteristics), whether to process (i.e., enhance some locations and not others), or type of processing (i.e., one type for detected anatomy or artifact and other type for other locations). For example, the locations of a detected artifact are filtered or scaled differently than other locations to suppress the artifact.

The display 60 is a monitor, LCD, LED, plasma, projector, printer, or other now known or later developed display device. The processor 62 and/or the image processor 58 generate display signals for the display 60. The display signals, such as RGB values, may be used by the processor 62.

The display 60 is configured to display an image representing the scanned region of the patient, such as a B-mode image. The image is generated from the image processed detected data. After the adaptive image processing is applied, an image is generated and displayed on the display 60. The image represents the scan region, but has intensities or estimated values that are altered to enhance or suppress based on the detected locations. The image is generated from the data after the image enhancement guided by the knowledge base detection. For example, a B-mode image with a detected artifact having been reduced is displayed. The reduction is partial or completely removed.

The memory 64 is a computer readable storage medium having stored therein data representing instructions executable by the programmed processor for image enhancement in medical diagnostic ultrasound. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method of image enhancement in medical diagnostic ultrasound, the method comprising:

acquiring, by an ultrasound system, ultrasound image data from a scan of tissue of a patient, the ultrasound image data representing spatial locations of the tissue;

applying, by a processor of the ultrasound system, a machine-learnt classifier to the ultrasound image data, the machine-learnt classifier having been trained with machine learning from a database of ground-truth annotated images, the machine-learnt classifier outputting first locations of an imaging artifact of the ultrasound system in the ultrasound image data in response to input of the ultrasound image data to the machine-learnt classifier;

altering the ultrasound image data for the first locations of the imaging artifact differently than for second locations, the altering enhancing anatomy at the second locations not associated with the imaging artifact more than the first locations of the imaging artifact; and displaying an ultrasound image of the tissue of the patient from the altered ultrasound image data.

2. The method of claim 1 wherein acquiring comprises acquiring B-mode image data after B-mode detection.

3. The method of claim 1 wherein applying comprises:
extracting input feature values from the ultrasound image data; and
outputting the first locations in response to input of the input feature values to the machine-learnt classifier.

4. The method of claim 1 wherein applying comprises detecting the first locations of the imaging artifact as locations of a grating lobe, and wherein altering further comprises applying a filter or amplitude scaling to the first locations of the imaging artifact and not at the second locations.

5. The method of claim 1 wherein applying comprises detecting the first locations of the imaging artifact as locations of spontaneous contrast of blood cells, and wherein altering further comprises amplitude scaling more greatly for or applying greater temporal persistence to the first locations of the imaging artifact than the second locations.

6. The method of claim 1 wherein applying comprises detecting shadowing, and wherein altering further comprises reducing the shadowing with an increase in intensity in the shadowing.

7. The method of claim 1 wherein altering comprises spatially adaptive filtering, the spatially adaptive filtering adapting as a function of the first locations of the imaging artifact.

8. The method of claim 1 further comprising:
outputting an indication of the first locations of the imaging artifact; and
performing the altering after receiving user confirmation based on the output indication.

9. The method of claim 1 further comprising:
detecting an anatomic structure represented in the ultrasound image data with an additional machine-learnt classifier; and
filtering the ultrasound image data based on the anatomic structure,
wherein displaying comprises displaying the ultrasound image from the altered and filtered ultrasound image data.

10. The method of claim 1 wherein displaying comprises displaying the ultrasound image with the imaging artifact reduced relative to the ultrasound image without the altering.

11. A non-transitory computer readable storage medium having stored therein data representing instructions executable by a programmed processor for image enhancement in medical diagnostic ultrasound, the storage medium comprising instructions for:

receiving, from an ultrasound scanner, detected ultrasound data representing a patient;

classifying locations represented by the detected ultrasound data as representing an artifact or anatomy, the classifying being with a knowledge base;

altering the detected ultrasound data as a function of the classification of the locations, the altering being an altering of amplitude of the ultrasound data for the artifact or anatomy differently relative to the amplitude of the ultrasound data for representing background, tissue, fluid and/or another object different than the classified artifact or anatomy while maintaining representation of all of the locations including representation of the background, tissue, fluid and/or the other object, the altering of the amplitude being by increase in amplitude, by spatial filtering, or by persistence; and generating an image from the enhanced ultrasound data as altered.

12. The non-transitory computer readable storage medium of claim 11 wherein classifying comprises classifying with the knowledge base comprising ground-truth labeled database of ultrasound data.

13. The non-transitory computer readable storage medium of claim 11 wherein classifying comprises classifying with a machine-learnt classifier, the machine-learnt classifier learnt from the database.

14. The non-transitory computer readable storage medium of claim 11 wherein classifying comprises detecting an anatomical structure as the anatomy, and wherein altering comprises the spatial filtering as a function of the locations of the anatomical structure.

15. The non-transitory computer readable storage medium of claim 11 wherein classifying comprises detecting the artifact, and wherein altering further comprises reducing the amplitude for the locations of the artifact.

16. The non-transitory computer readable storage medium of claim 11 wherein receiving comprises receiving B-mode data, wherein altering comprises the spatial filtering, and wherein generating the image comprises generating a B-mode image without segmentation.

17. A system for image enhancement in medical diagnostic ultrasound, the system comprising:

a receive beamformer configured to acquire ultrasound data representing a region of a patient;

a B-mode detector, Doppler estimator, or both configured to output detected data from the ultrasound data;

a processor configured to extract input features from the detected data, identify an artifact from the detected data as a function of a knowledge base, and image process the detected data as a function of the artifact, the image process including processing the detected data for locations of the artifact differently than other locations where the other locations are enhanced more than the locations of the artifact; and a display configured to display an image of the region based on the image processed detected data, the image being an ultrasound image with the artifact reduced.

18. The system of claim 17 wherein the processor is configured to identify with a machine-learnt classifier derived from the knowledge base.

19. The method of claim 1 wherein enhancing comprises emphasizing an edge or border of the anatomy with less emphasizing of an edge or border of the imaging artifact.

* * * * *